(12) United States Patent
Srinivasan et al.

(10) Patent No.: US 8,771,517 B2
(45) Date of Patent: Jul. 8, 2014

(54) IC SYSTEM INCLUDING SAMPLE PRETREATMENT AND USING A SINGLE PUMP

(75) Inventors: Kannan Srinivasan, Tracy, CA (US); Rong Lin, Sunnyvale, CA (US)

(73) Assignee: Dionex Corporation, Sunnyvale, CA (US)

( * ) Notice: Subject to any disclaimer, the term of this patent is extended or adjusted under 35 U.S.C. 154(b) by 1155 days.

(21) Appl. No.: 12/702,880

(22) Filed: Feb. 9, 2010

(65) Prior Publication Data

US 2010/0139376 A1 Jun. 10, 2010

Related U.S. Application Data

(62) Division of application No. 11/229,031, filed on Sep. 16, 2005, now Pat. No. 7,682,506.

(51) Int. Cl.
*B01D 15/08* (2006.01)

(52) U.S. Cl.
USPC ........................................ 210/656; 210/198.2

(58) Field of Classification Search
USPC .............. 210/635, 656, 659, 748, 198.2, 243; 205/789, 792; 422/70; 436/161
See application file for complete search history.

(56) References Cited

U.S. PATENT DOCUMENTS

| | | | |
|---|---|---|---|
| 5,042,293 A | 8/1991 | Heyde | |
| 5,352,366 A | 10/1994 | Courtaud et al. | |
| 6,225,129 B1 | 5/2001 | Liu et al. | |
| 8,101,422 B2 * | 1/2012 | Srinivasan et al. | 436/161 |
| 2003/0017611 A1 | 1/2003 | Vanatta | |

FOREIGN PATENT DOCUMENTS

WO WO98/40145 9/1998

OTHER PUBLICATIONS

P.R. Haddad et al., *J. Chromatogr.* A. 856 (1999), 145-177 ("Developments in sample preparation and separation techniques for the determination of inorganic ions by ion chromatography and capillary electrophoresis").
R.M. Montgomery et al., *J. Chromatogr.* A 804 (1998) 55-62 ("On-line sample preparation techniques for ion chromatography").

* cited by examiner

*Primary Examiner* — Ernest G Therkorn
(74) *Attorney, Agent, or Firm* — Timothy J. Ohara

(57) ABSTRACT

An IC system including sample preparation. The system includes a liquid sample injection loop, an ion concentrator, an ion separator, and only a single pump for pumping fluid through the system.

7 Claims, 11 Drawing Sheets

IC SYSTEM INCLUDING SAMPLE PRETREATMENT AND USING A SINGLE PUMP

CROSS-REFERENCE TO RELATED APPLICATIONS

This application is a divisional of U.S. application Ser. No. 11/229,031 filed on Sep. 16, 2005, now U.S. Pat. No. 7,682,506.

BACKGROUND OF THE INVENTION

Monitoring the presence of corrosive ions is routinely done in the semiconductor and power industries. For detecting trace ions in ultra pure water (UPW) a large volume of the sample stream is concentrated into a concentrator column for further analysis. Typically an external sample stream pump is used to dispense the sample and route it through the concentrator column. These sample pumps typically are low cost and do not provide good flow control, resulting in variances in peak response and subsequently poor quantitation. Another potential problem is deterioration of the pump components due to their exposure to the sample stream. Also, changing sample streams can lead to contamination due to carry over. It would be useful to provide a low cost solution to the above problems.

The sample loop size in IC applications are chosen based on the required detection sensitivity for the ions of interest. Larger loops are typically used to detect low ppb level of ions. In some cases, the sample concentrations vary so much that there is a need to switch from a small loop size (e.g., ppm level of ions) to a larger loop size (e.g., ppb level of ions). With current instrumentation it is cumbersome to replace the loops and this is typically done manually.

From an operation perspective, mixing the sample zone with the eluent should be minimized to avoid poor peak shapes for the early eluting peaks, particularly while using large loop injection. It would be useful to have a method that would allow for sensitive detection of analytes of interest without changing the sample loop size.

It can be cumbersome to make large volume loops that are substantially stable under the high pressure requirements of the IC system. For a selected volume, the length of the tube increases with decreasing inner diameter of the sample loop tubing and the pressure rating decreases when the diameter of the tubing increases substantially.

In other applications with a large sample loop size, the void volume due to the large loop injection may result in a large baseline upset from the void and this affects the baseline integration of peaks eluting close to the void. For loop sizes significantly larger than the column volume, the large volume of unretained components such as water that traverse the entire column can cause problems of equilibration within the column and lead to undesirable baseline shifts and wander. This can lead to inaccuracies in peak integration and quantitation. It would be useful to eliminate the above discussed effects of large loop injections.

In neutralization applications, the sample slug is passed into the neutralizer device following which the neutralized sample is diverted into a concentrator column. A pump is used in the above application for the purpose of pumping a DI water stream that carries the sample slug through the neutralizer and for subsequent preconcentration. The above setup requires an additional pump and suffers from some of the limitations discussed above. It would be useful to eliminate this additional sample stream pump and reduce the overall cost of the IC system.

Another area of sample preparation is matrix ion removal. Frequently with environmental samples, the analyte of interest is overwhelmed by matrix ions, and it is difficult to get good quantitative information. Under these conditions, a matrix ion elimination step may be needed. Similar to the neutralization application discussed above, a DI water pump is used to load the sample and divert it through a matrix ion elimination column and subsequently load the sample onto a concentrator column.

It would be useful to reduce the overall cost of an IC system.

Another area of sample preparation is in converting the sample to various forms prior to analysis. Similar to the above discussed applications this setup may also require a DI water pump. Here again it would be useful to reduce the overall cost of an IC system by eliminating the need for this pump.

SUMMARY OF THE INVENTION

In accordance with one embodiment of the present invention, ion chromatography apparatus is provided comprising: (a) a liquid sample injection loop, (b) an ion concentrator including ion concentration medium for retaining ionic species, (c) an ion separator comprising ion separation medium, (d) a first conduit providing fluid communication between said loop and said concentrator, (e) a second conduit providing fluid communication between said concentrator and said ion separator, (f) valving including the following modes: (1) a first mode in which one of said sample loop ports is open to fluid communication with a liquid sample source, flow is blocked between said sample loop and said concentrator, and said concentrator is in fluid communication with said ion separator through said second conduit, and (2) a second mode in which said sample loop is in fluid communication with said ion concentrator through said first conduit, and (g) a single pump only in said apparatus for pumping fluid through said first and second conduits which are in fluid communication in said first and second modes.

A further embodiment is an ion chromatographic method comprising: (a) flowing an aqueous liquid stream from an aqueous liquid source through a sample loop containing a liquid sample including ions of interest, (b) flowing the step (a) effluent through concentrator ion exchange medium in an ion concentrator to retain said sample ions, (c) flowing an eluent through said concentrator ion exchange medium to remove said retained sample ions in a concentrator effluent, (d) flowing the step (c) effluent through ion separation medium in an ion separator to separate said sample ions and form an ion separation effluent, and (e) flowing the step (d) effluent past a detector to detect the separated sample ions, the flow in steps (a) through (d) being performed under pressure applied by a single pump.

DETAILED DESCRIPTION OF THE PREFERRED EMBODIMENTS

The present invention relates to ion chromatography apparatus which includes only a single pump for pumping fluid through the ion chromatography apparatus. The system includes a pump, a liquid sample injection loop, an ion concentrator, an ion separator comprising ion separation medium, valving, and at least one detector. Optionally, a suppressor may be included in the above setup. Also, a suitable sample delivery device such as an auto sampler may be used in the above setup to load the sample. As used herein, the term "single pump" does not exclude the possible use of a pump external to the IC system, such as one which may be used in the sample delivery device.

Figure 1:
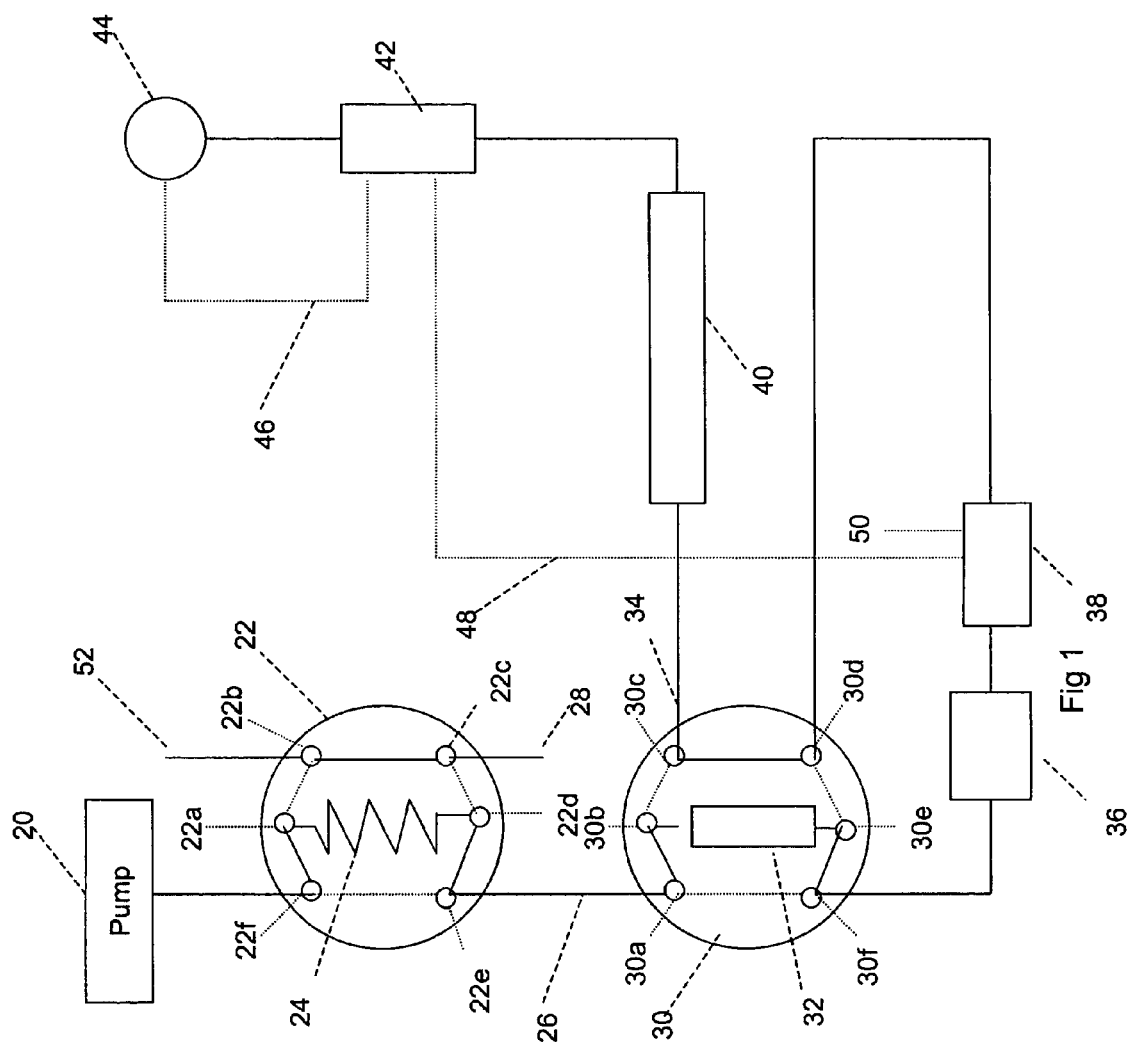
FIGS. 1-4 and 6-8 are embodiments of systems according to the present invention.

The invention will first be described with respect to one embodiment of the present invention as illustrated in FIG. 1. As used herein, the term "valving" refers to one or more valves that serve the function of changing the fluid flow path through the system by use of various valve settings, also referred to as modes herein.

Referring to FIG. 1, an aqueous liquid stream, preferably containing water and more preferably deionized (DI) water, is pumped from a source, not shown, by pump 20 suitably of the type GP50 sold by Dionex Corporation, to valve 22. In the embodiment of FIG. 1, the valving comprises two six port valves namely 22 and 30. Pump 20 is directly upstream from the sample injection loop 24, meaning there is no intermediate modules such as an eluent generator between the pump and sample injection loop.

In the first sample loop loading mode, sample, from an autosampler 52, not shown, suitably one supplied by Dionex Corporation under the name _AS50, is directed to six-way valve 22, suitably one supplied by Upchurch Scientific having six ports 22*a-f*. During sampling, the sample enters valve 22 through port 22*b* and flows through port 22*a* through sample loop 24 installed between the ports 22*a* and 22*d* and from there through ports 22*d* and 22*c* and to waste 28. During sample loading onto loop 24, pump 20, pumps the aqueous liquid into port 22*f* which flows out of valve 22 through port 22*e*, bypassing sample loop 24. From there, the aqueous solution flows in line 26 to valve 30, the second valve in the valving of FIG. 1, which includes six ports 30*a-f*. Concentrator column 32 is plumbed to the valve 30 via ports 30 *b* and 30 *e*, and is suitably of the type sold by Dionex Corporation under the designation TACLP1. During loading of sample loop 24, the aqueous solution exiting from port 22*e* flows into valve 30 in port 30*a*, bypasses concentrator column 32, and flows out port 30*f* in line 34. From there, the solution flows out the system through eluent generator 36, gas removal device 38, back to ports 30*d* and through the concentrator column 32 and flows out of port 30*c* and is routed through chromatography column 40, suppressor 42 and detector 44 as will be described hereinafter. This first position of the valving comprising valves 22 and 30 is referred to as the first valve mode or first valve setting or position. This mode is essentially used to load the sample into the sample injection loop and hence the position of the valve 30 is not critical but it is preferred to maintain the above plumbing configuration.

In a second mode or setting of the valving, valve 22 is switched to load the concentrator column 32. Here, the sample flow through ports 22*b* and 22*c* and to waste 28, bypassing the sample loop 24. The aqueous solution under pressure from pump 20, flows through ports 22*f* and 22*a* to carry the sample previously loaded in sample loop 24 out ports 22*d* and port 22*e* and via line 26 into port 30*a* of valve 30. From there, the solution flows through port 30*b* and concentrator column 32, out port 30*e* through port 30*f* and to line 34. From there, the solution flows through the system as in the first mode except the liquid flows directly from port 30*d* to 30*c* and bypasses the concentrator column 32 and is routed out to column 40. The primary function of this mode is to load the sample into the concentrator column.

In a third mode, solution from the pump is routed into the valve 22 and may or may not bypass sample loop 24 and exits out of port 22*e* and is routed through line 26 into valve 30. If the sample loading is done as outlined in the first mode then the solution from the pump bypasses the sample loop 24. In valve 30 the solution bypasses concentrator column 32 and is directly routed via port 30*f* to eluent generator 36. The eluent generated is routed through the degas module 38 and is then routed back to valve 30 at port 30*d* and is used to elute the retained species from the concentrator column 32. The eluent is then routed out of the valve via port 30*c* and is routed to column 40 via line 34 for further analysis similar to a standard conventional IC system. This mode is essentially used to elute the retained sample from the concentrator column.

The sample ions of interest are directed from sample loop 24 to concentrator column 32 where they are retained by ion exchange resin therein while the carrier solution from pump 20 flows out through the system. The cycle of the first and second modes can be repeated to concentrate multiple sample loop volumes in concentrator 32 to enrich the sample. Specifically, sample ions in the sample loop 24 can be rerouted to concentrator column 32 multiple times so long as the capacity of concentrator column 32 is not exceeded, thus the effecting sample enrichment by multiple loop injections. When the desired number of sample slugs has been loaded into concentrator column 32, eluent generated in eluent generator 36 flows through concentrator column 32 to elute the sample from column 32 and carry it to separator 40. From there, the system operates as in a conventional ion chromatography system.

Figure 9:
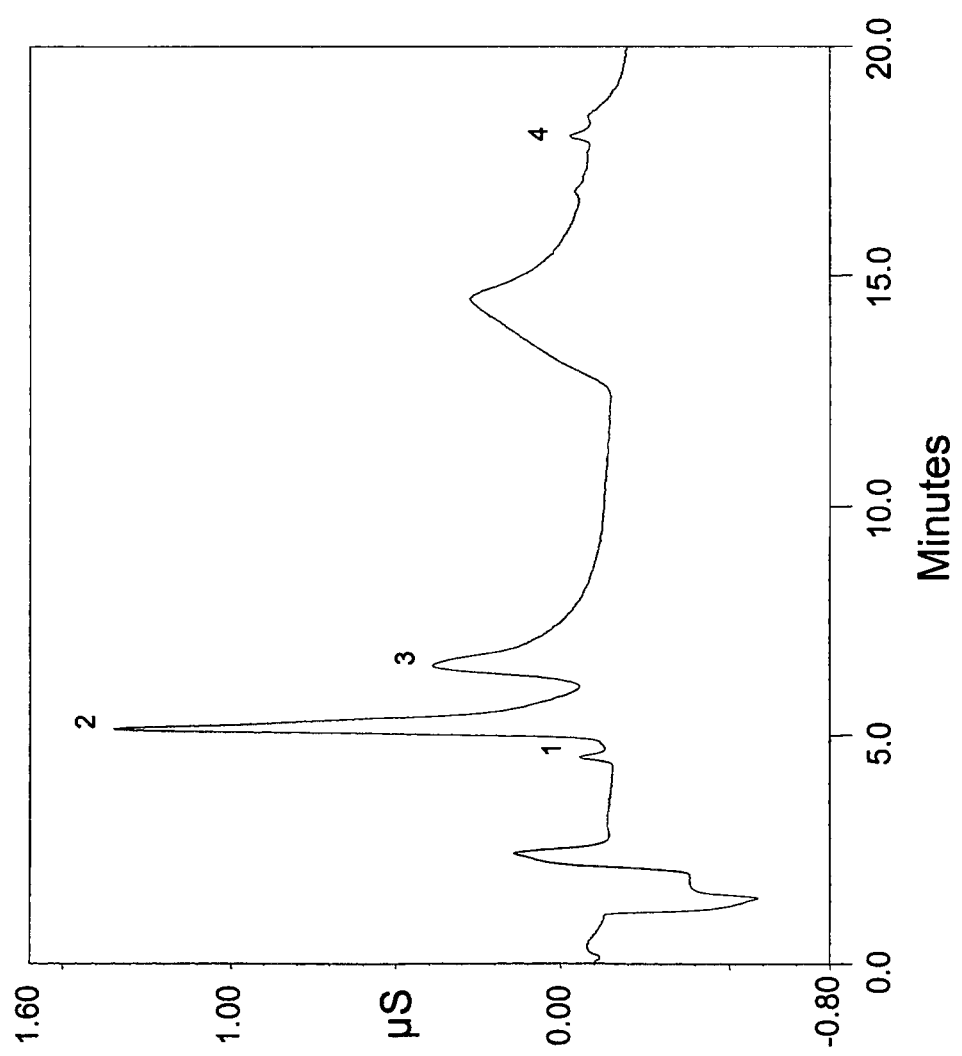

The eluent generator 36 may be of the type set forth in U.S. Pat. No. 6,225,129 and sold by Dionex Corporation. Optional or gas removal degas module 38 may be of type sold by Dionex Corporation under the designation EG degas module. An optional continuous regenerated trap column, not shown, sold by Dionex Corporation under the designation CR-TC, may be disposed down stream of eluent generator 36 to purify the flowing liquid prior to flowing to module 38 to remove electrolytic gases from the eluent. The sample in the eluent stream is pumped from valve 30 through column 40, suppressor 42 and detector 44 which may be of a conventional type such as described in U.S. Pat. No. 5,352,366. As illustrated, suppressor 42 is a membrane suppressor of the type disclosed in the same patent in which the detector effluent is recycled in line 46 to a regenerant flow channel separated from a sample stream flow channel by a permselective membrane, not shown. The effluent from the regenerant flow channel can be recycled in line 48 to the degas module to carry away the gases generated in the eluent generator 36. Gas removal module 38 comprises a flow-through chamber consisting of a porous membrane such as a fluorocarbon polymer such as PTFE, ETFE, PFA or FEP separating an eluent channel from an outside waste channel. The gases flow from the eluent channel to the outside channel and is carried with the solution flowing in from line 48 and exits the device carrying with it the electrolytic gases via line 50. Gas removal modules are suitably of the type illustrated in FIG. 9 of U.S. Pat. No. 6,225,129.

In the illustrated embodiment, the ion chromatography system includes a suppressor 42 and so the analysis typically is termed suppressed ion chromatography, suppressed IC or, simply, IC. Alternatively, suppressor 42 may be eliminated. An optional trap column, not shown, of the anion exchange or cation exchange resin bed type or a combination, not shown, can be added in line 34 to remove any residual ionic contaminants in the line. During anion analysis, the stream used for eluent generation should be substantially free of anionic contaminants. Thus, for anion analysis, it is preferable to place an anion exchange trap column in line 34, not shown, if substantial amounts of anion contaminants are expected in this stream. The location of the trap column could be before or after eluent generation in line 34. A suitable trap column is of the type sold by Dionex Corporation under the name ATC-HC for anion applications. A continuously regenerated trap column, e.g., of the CR-ATC type, could be used in place of the ion exchange resin type of trap column for anion applications.

Preferably, pump 20 is directly upstream from sample injection loop 24. By this, it is meant that there is no intervening eluent generation device or chromatography column between pump 20 and the sample injection loop 24. Also, pump 20 preferably provides the pressure for pumping fluids through the conduits of the system in all modes and, in general, to perform all the operations of the ion chromatography system.

Conduit 26 provides fluid communication between sample loop and concentrator column 36. Also, conduit 34 provides fluid communication between concentrator 32 and ion separator 40. When the term "fluid communication" is used in this context, this means that the fluid flows through one or more to the conduits or tubing either directly between these components or through intermediate components. Further, the term "conduit" encompasses a conduit within or integrated with a valve. In other words, fluid communication between two components means that fluid can flow from one component to another but does not exclude an intermediate component between the two recited components which are in fluid communication.

One advantage of the present system is that concentrator column 32 is only exposed to the aqueous solution, preferably DI water, during loading so that the analytes remain focused on the concentrator column 32. Thus, it is possible to pursue concentration or enrichment on column 32 while performing a chromatography run. In other words, the system of the present invention permits sample preparation by concentration column 32 or other sample preparation techniques without affecting the chromatographic run. Another advantage of this system is that pump 20 is not exposed to the eluent generated in eluent generator 36 and so is protected from essentially corrosive acid or base eluent.

Figure 2:
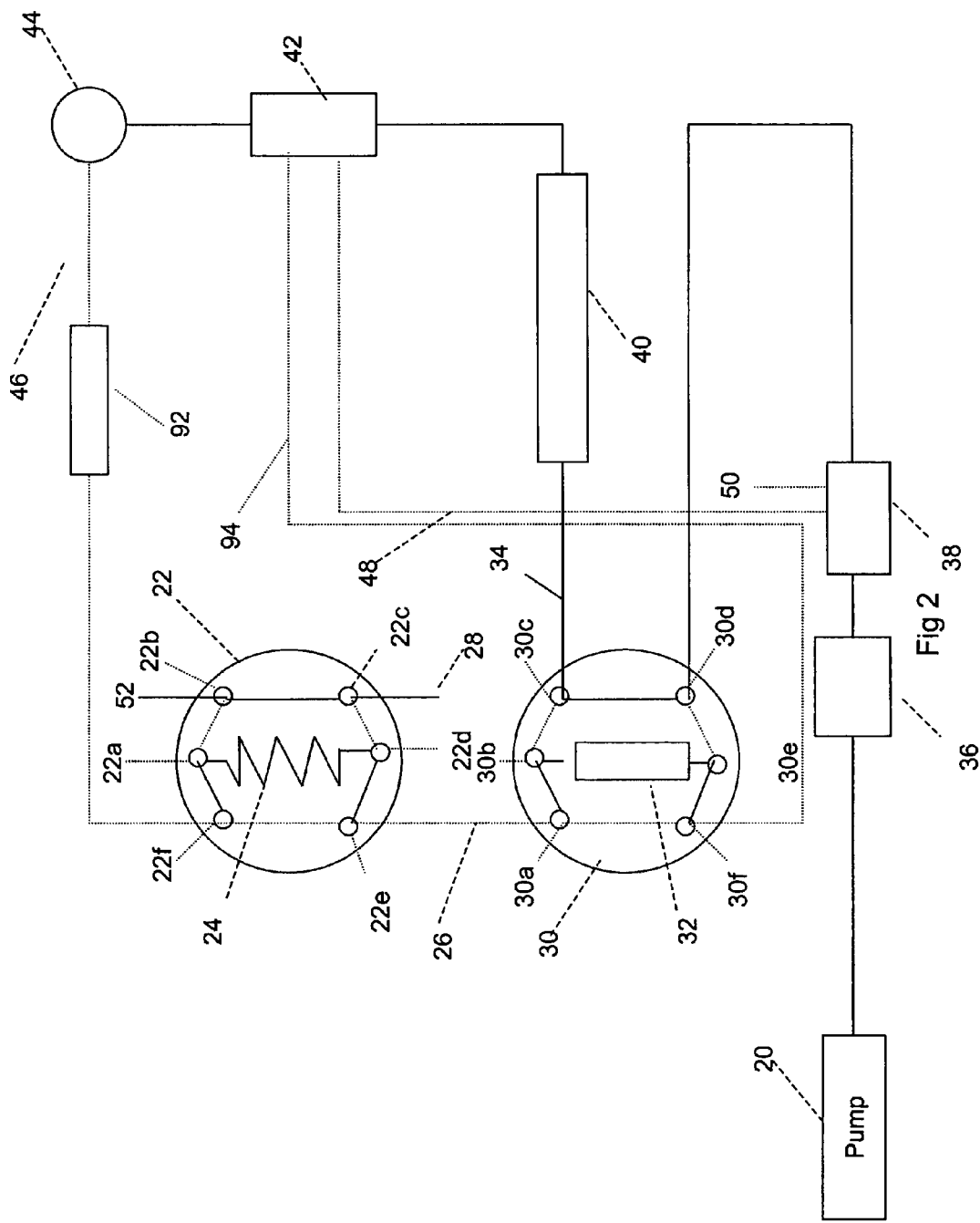

Another embodiment is illustrated in FIG. 2. Like parts for FIGS. 1 and 2 will be designated with like numbers. Here, chromatographic analysis could be performed using either manually prepared eluent or eluents prepared by an eluent generator. Referring to FIG. 2, in the first mode pump 20 pumps an aqueous liquid stream, preferably DI water, which is diverted into eluent generator cartridge 36 and gas removal module 38. As with the embodiment of FIG. 1, an additional trap column, sold by Dionex Corporation under the name CR-TC can be used to purify the eluent or DI water stream. The generated eluent flows to valve 30 through port 30d and then through port 30c to chromatographic column 40 via line 34 and to the sample flow channel, not shown, of suppressor 42 and to detector 44. This portion of the system is similar to a conventional compressed IC system and to the system of FIG. 1.

The effluent from detector 44 is routed by line 46 to a trap column 92, suitably of the type discussed above, e.g., an exchange resin bed. It functions to purify the effluent from detector 44. Also, as discussed above, a continuously regenerated trap column can be used in place of the trap column such as an anion exchange column sold by Dionex Corporation under the name TAC-LP1. The purified eluent from trap 92 is then directed to valve 22 through port 22f. An autosampler 52 loads the sample into sample loop 24 through ports 22b and then port 22a and flows out port 22d to port 22c to waste.

In the second mode, the purified effluent stream from detector 44 and trap 92 is directed into sample loop 24 to load the sample in concentration column 32 by flow through port 22f and 22a, loop 24 and out port 22d to port 22e and line 26 to valve 30. In this second mode, the sample plug is diverted into concentrator column 32 where the sample is retained and the effluent flows out port 30e and port 30f in a recycle line 94 which can be used as the regenerant solution in the regenerant flow channel, not shown, of suppressor 42 to exit in line 48 which can be used as a carrier liquid stream to carry the gas away in optional in gas removal device 30 to waste in line 50. As in FIG. 1, the sample ions are focused in concentrator column 32.

In the third mode, the eluent stream including the eluent generated in eluent generator 36 flows into valve 30 through ports 30d and 30e through concentrator column 32 and out ports 30b and 30c to column 40 for separating the sample ions. In this mode, the effluent from trap 92 flows through ports 22f and 22e of valve 22 to ports 30a and 30f of valve 30 and through line 94 to the regenerant flow channel of suppressor 42 and to waste.

As discussed in the following embodiments a concentrator column is typically used to concentrate the species of interest. The function of this column is to concentrate the sample as a slug. The concentrator column dimensions are typically 4 to 6 times smaller than the analytical column. A chromatographic or analytical column is used to separate species and generally has a much higher capacity than the concentrator column. The function of the analytical column is to separate species where as the function of the concentrator column is to concentrate species. In typical operation the concentrator column is loaded with the sample in one direction and the sample is eluted in a small slug in the reverse direction.

A trap column is usually used to trap contaminants from a flowing stream. For example during anion analysis with hydroxide eluents an anion exchange trap column may be used to eliminate anionic contaminants such as carbonate or chloride.

A converter column as defined in the following embodiments is a column used to convert the sample stream or slug into other forms. Thus the converter column does not concentrate or retain the sample rather it is used to convert the sample to another form. For example during anion analysis of weak acids it may be preferable to convert the sample to the salt form using a converter column comprising of cation exchange resin in the sodium form. In this example the counter ions to the sample anions are all converted to the sodium form.

A matrix elimination column as used herein eliminates the matrix ions of the same charge as the sample ions. The matrix elimination step could be a matrix diversion or matrix retention step. In the matrix diversion step the matrix is diverted selectively versus the sample ions. In the matrix retention step the matrix is selectively retained in comparison to the sample ions.

A neutralizer column is a column that converts the matrix ions to a weakly dissociated form. Although it is a matrix elimination column the column operates by retaining the counter ion of the sample ion. As used herein, neutralization means converting a acid or base matrix in a sample to a weakly dissociated species while converting the sample to the base or acid form. For example when analyzing trace anions in sodium hydroxide base, the sodium hydroxide is neutralized to a weakly dissociated water by exchanging the sodium for hydronium ions from the neutralizer column. The trace anions are converted from the salt form to acid form. A neutralizer serves the function of reducing the interference of acid or base matrices present in a sample.

Figure 3:
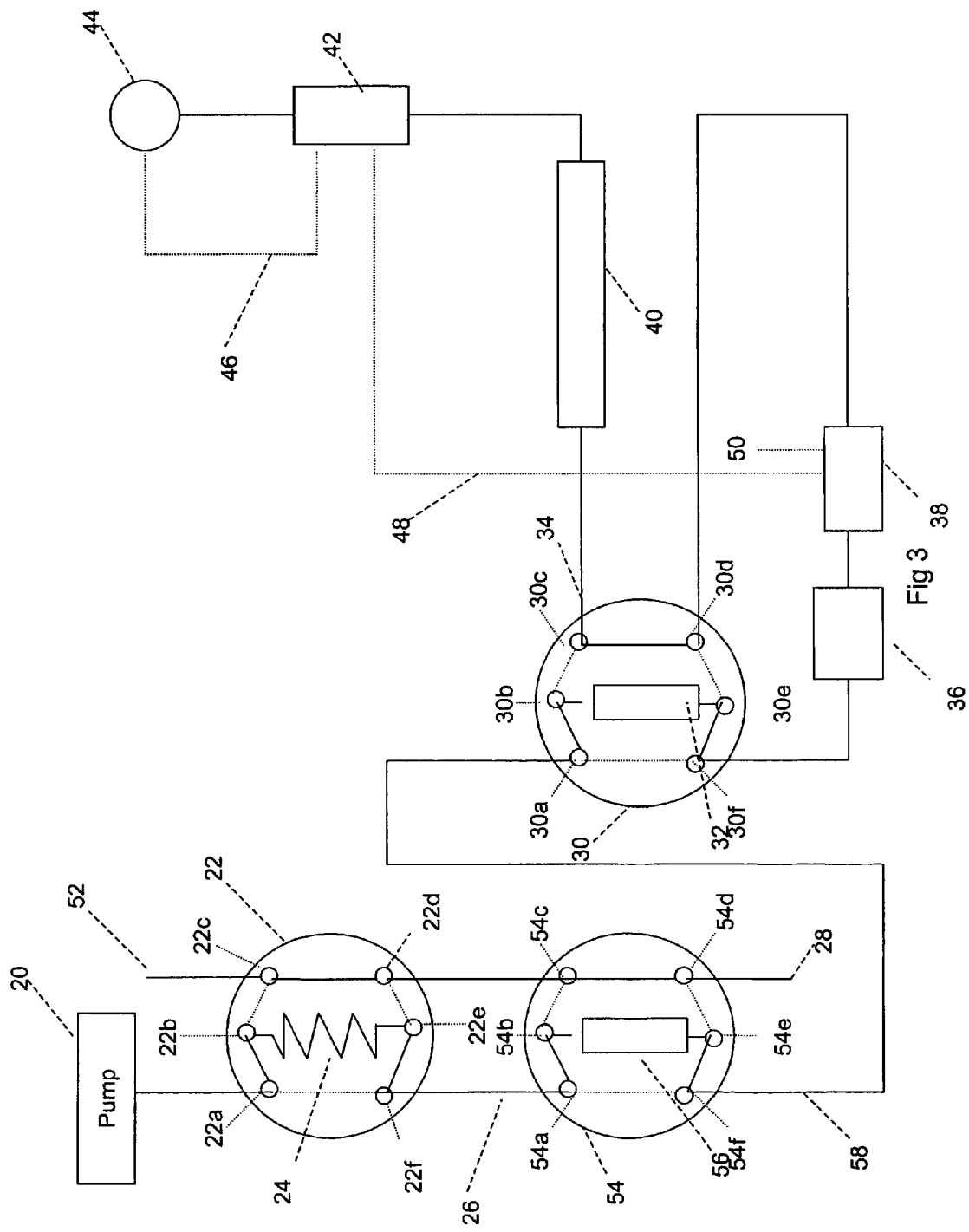

FIG. 3 illustrates another embodiment of the present invention. In this instance, the valving includes three six-way valves, a valve 54 in addition to valves 30 and 22 discussed above. Like parts will be designated with like numbers. Valve 54 includes six ports 54a-e. In this example, the sample is neutralized using an ion exchange bed column neutralizer 56 located on valve 54 and plumbed between ports 54b and 54e. A suitable neutralizer can be a 4×50 mm column packed with ion exchange resin e.g. during neutralization of a base sample a sulfonated resin such as sold under the trademark Dowex 50WX8 resin or Dionex ASC resin can be used to pack the above neutralizer.

The DI water from pump 20 is routed through six port valve 22 with the sample loop 24 as in the embodiments of FIGS. 1 and 2. Also, as in such embodiments, the loop is filled with the sample via auto sampler 52 during the load step. In the inject step for valve 22 and 54, the sample loop 24 is in line with the DI water stream from pump 20 which diverts the contents of loop 24 through neutralizer column 56 on valve 54 by flow through ports 54a and 54b through the neutralizer column 56 and out ports 54e and 54f. In the load position of valve 54, neutralizer column 56 is in fluid communication with the autosampler 52 and can be regenerated by dispensing one or more regenerant streams from autosampler 52. For example, after the neutralizer column capacity is depleted, the neutralizer will be in the sodium form and will no longer be useful for neutralizing the base samples. Regeneration of the column can be accomplished by pumping an acid regenerant stream from the autosampler 52 through the neutralizer column. A DI water rinse can also be incorporated to ensure that there are no acid residues left in the neutralizer. The neutralizer can then be switched back to the inject state to neutralize samples.

The sample stream is diverted from neutralizer 56 into concentrator column 32 in valve 30 as described in the previous embodiments. More specifically the sample slug is diverted out of the valve 54 via port 54f and conduit 58 and is diverted to valve 30. During the sample concentration step the sample slug is diverted via port 30a and 30b to concentrator column 32 for concentrating the sample and the DI water stream is then routed via 30e and 30f to the eluent generator module 36 for generating the eluent. The plumbing here on is similar to what was described for FIG. 1. The eluent is then routed through a degas module to remove the electrolytic gases and is then routed back to valve 30 via 30d and 30e to column 40 via line 34 and then the eluent is routed to a suppressor 42 and conductivity cell 44 and so on. It should be noted that the above sample loading, neutralization and sample concentration steps can be repeated multiple times to effect enrichment of the sample ions.

During the sample elution step, the DI water stream from conduit 58 is routed via 30 a directly to 30f and is routed via the eluent generator module 36 and degas module 38 to port 30d on valve 30. The eluent is then routed via 30e through the concentrator column 32 to elute the retained ions and is then routed via 30b and 30c to column 40 for separating the components.

The sample is eluted from concentrator column 32 and separation and detection are performed in a manner similar to conventional IC systems and to the flow system of FIG. 1. Thus, sample neutralization analysis can be employed in the system still only using a single pump.

Figure 4:
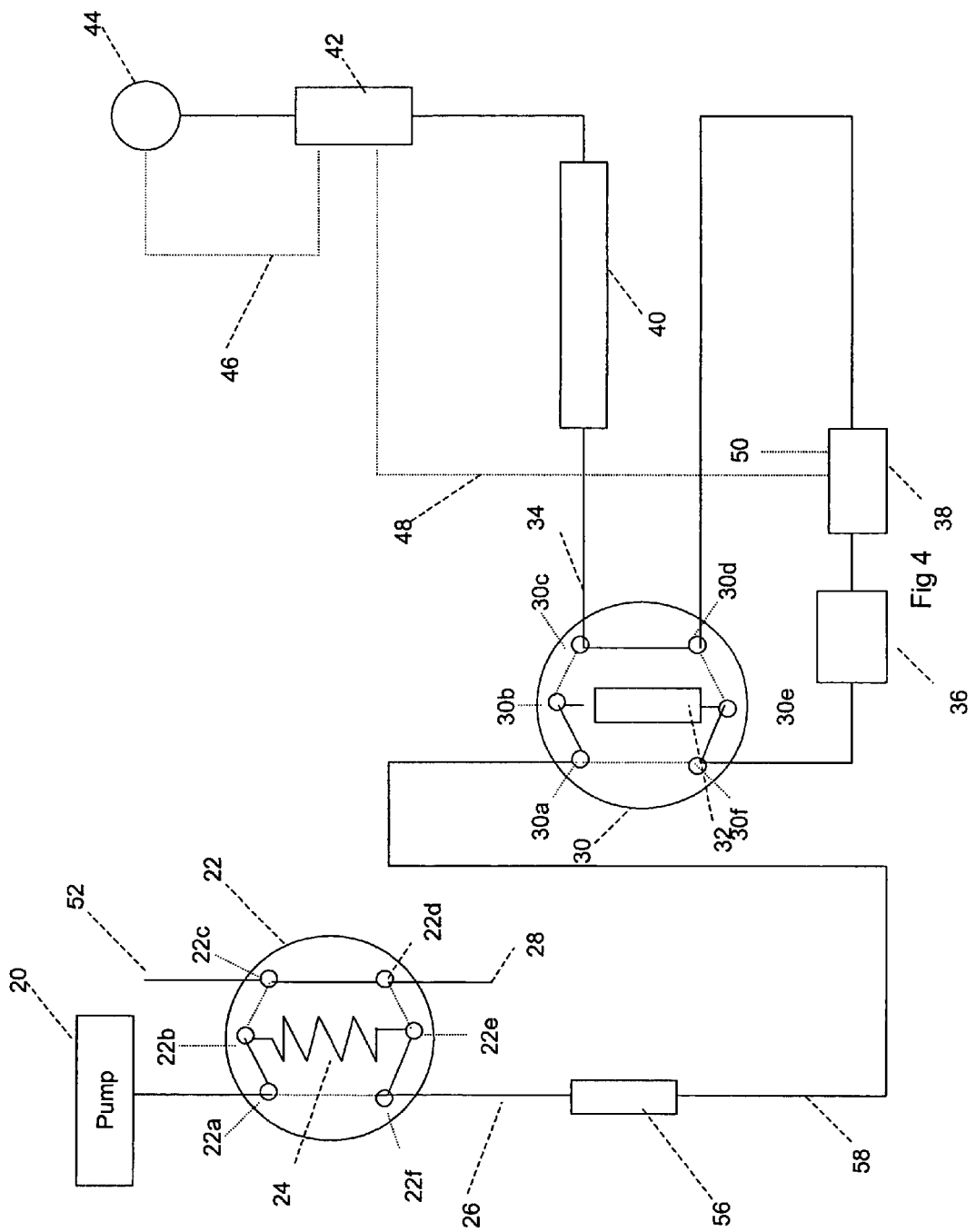

FIG. 4 is another embodiment of the invention similar to FIG. 3. Like parts will be designated with like numbers. Here, neutralizer 56 is used as in FIG. 3 without a valve 54 and is directly connected inline. Conduit 26 extends from valve 22 to neutralizer 56 and conduit 58 extending from neutralizer 56 to valve 30. Here, the neutralizer is manually taken off line upon depletion of its capacity. Other features of this embodiment are the same as those of FIG. 3.

Figure 6:
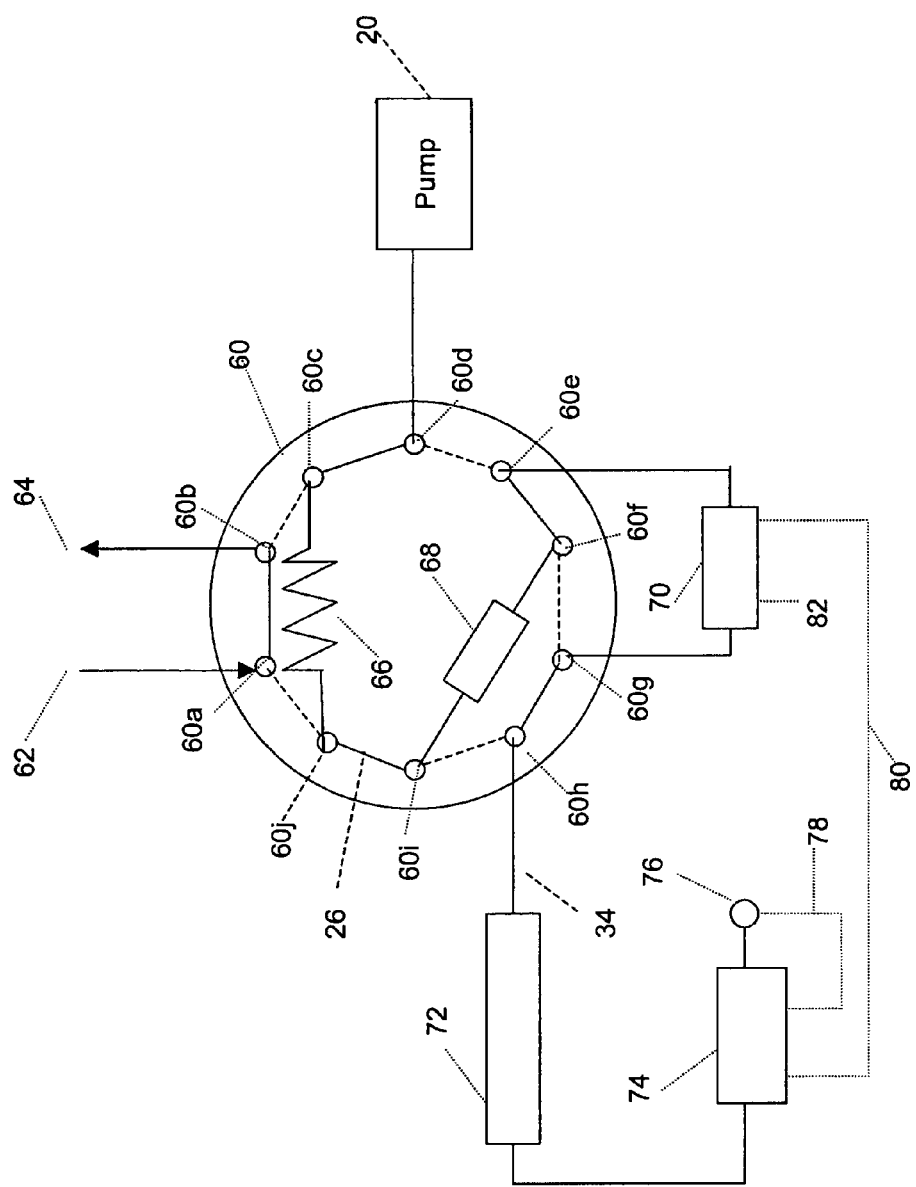

Referring to FIG. 6, another embodiment of the invention is illustrated in which the valving comprises a single ten port valve 60 with ports 60a-60j. Valve 60 includes a concentrator column 68 similar to concentrator column 32, a chromatography column 72 similar to chromatography column 40, a suppressor 74 similar to suppressor 42, an eluent generator/gas removal module 70 which is depicted here as a combination of eluent generator 36 and gas removal module 38, and a sample injection loop 66 similar to sample injection loop 24, all as in FIG. 1. In the sample loop load step, the autosampler 62 loads the sample into sample loop 66 and is diverted to waste 64. Sample flow is through ports 60a and 60j, loop 66, and ports 60c and 60b to waste at 64. During the load step, pump 20 dispenses the aqueous liquid, DI water, into valve 60 which passes through ports 60d and 60e through module 70, ports 60g and 60f through concentrator column 68 to elute the sample and then via ports 60i and 60h and via line 34 through chromatography column 72, suppressor 74 to detector 76, recycle 78 to suppressor 74 and then to module 70 to supply a carrier liquid stream as in FIG. 1. An eluent is generated in module 70.

During the injection step (shown with a dark line), the sample is displaced out of sample loop 66 by flow from pump 20 through port 60d, 60c, loop 66, port 60j, line 26 and port 60i through concentrator column 68, ports 60f and 60e through eluent generator/gas removal module 70 and is routed via port 60g and 60h to the chromatography column 72 suppressor 74 to detector 76, recycle 78 to suppressor 74 and then to module 70 to supply a carrier liquid stream as in FIG. 1. This configuration allows for trace enrichment using a single loop cycle.

Figure 7:
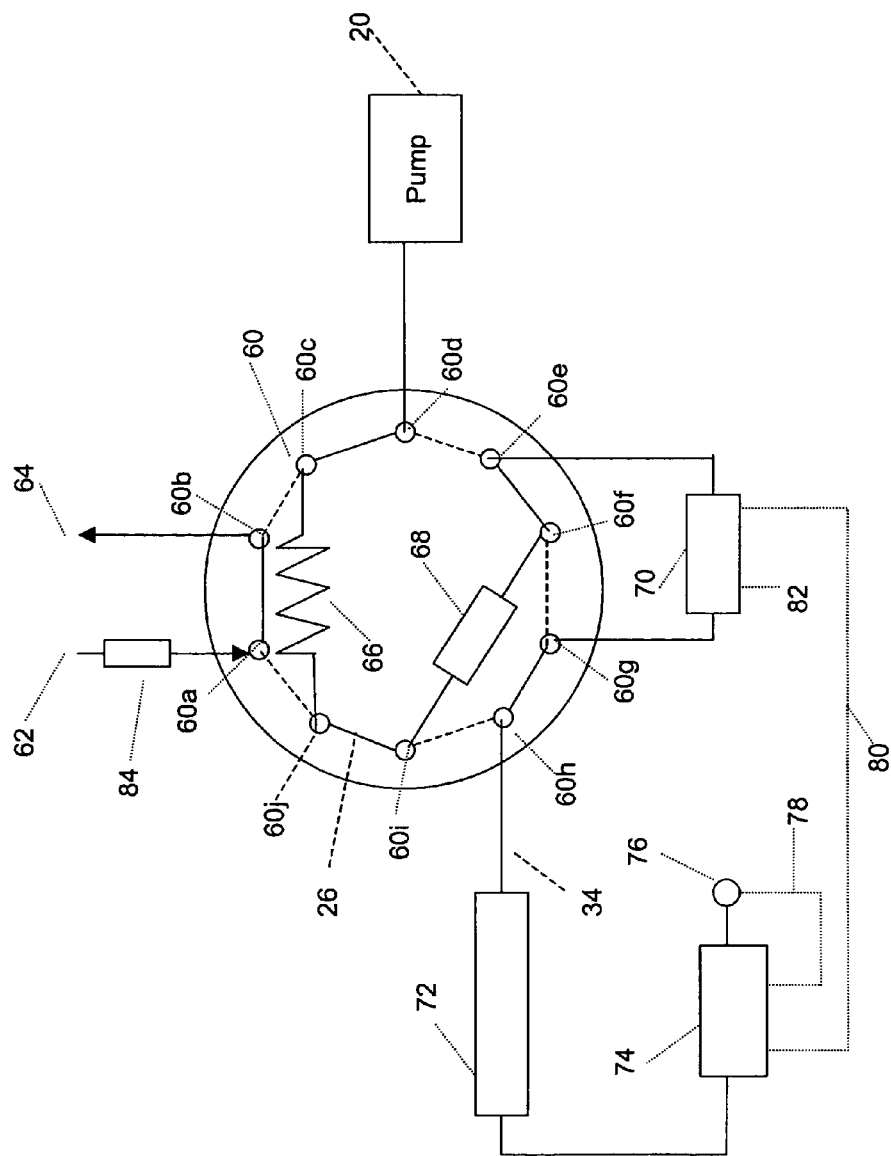

Referring to FIG. 7, another example is illustrated for sample pretreatment or matrix elimination. This system is similar to the system of FIG. 6 and like parts will be used to designate like numbers. In this system, a neutralizer column 84 disposed downstream of auto sample 62 and before valve 60. The sample in this case is neutralized before loading onto the sample injection loop and is then enriched on the concentrator column.

Figure 8:
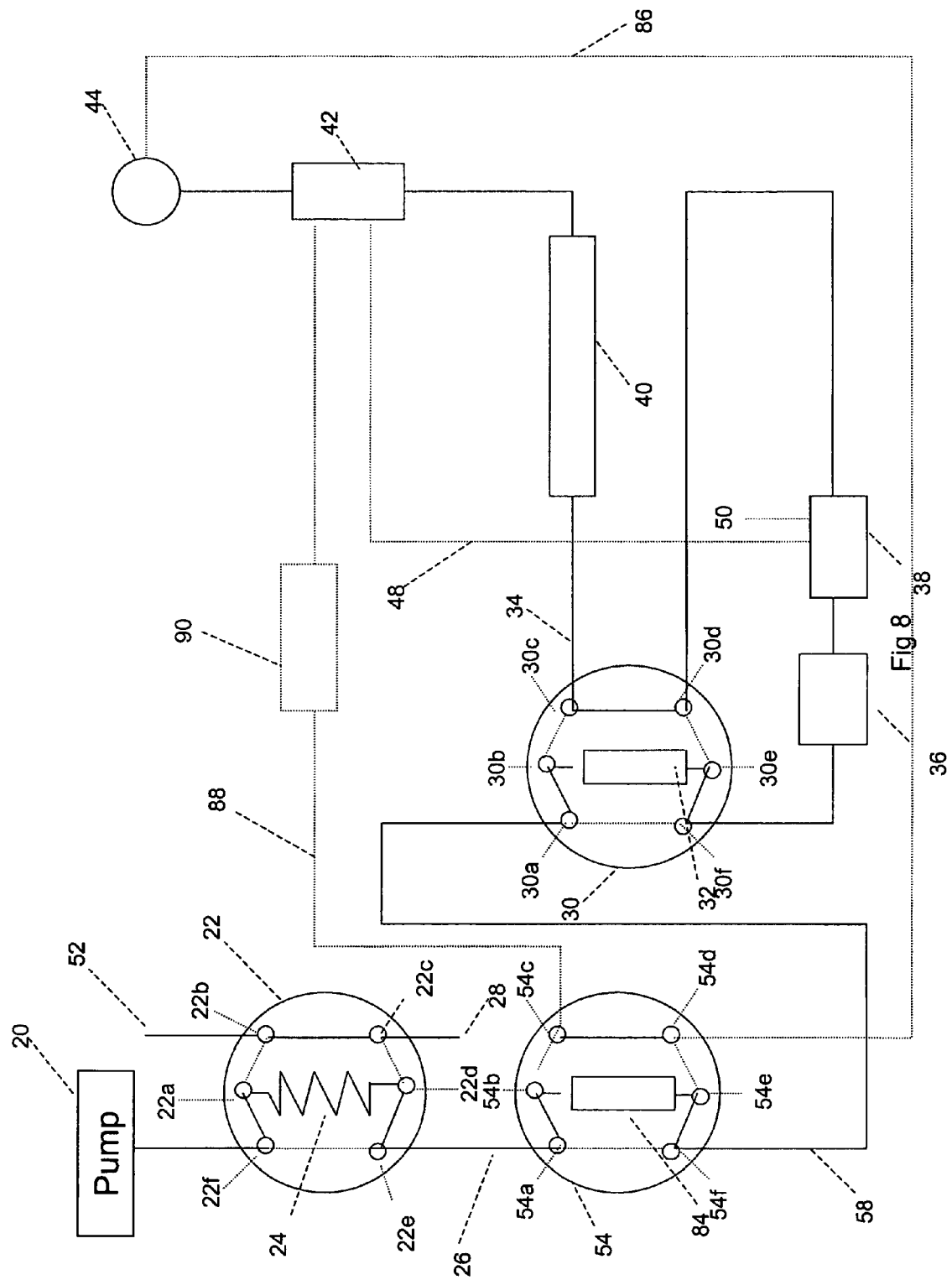

Referring to FIG. 8, another system for sample pretreatment or matrix elimination is illustrated. Like parts for FIGS. 3 and 8 will be designated with like numbers. In operation, the sample is loaded into sample loop 24 on valve 22 using autosampler 52 as in FIG. 1. In the inject position of valve 22, the sample is carried by the aqueous stream from pump 20 through loop 24, also as set forth in FIG. 1 to carry sample plug from the loop routed through a matrix elimination device, in this instance, ion exclusion column 84. Ion exclusion column retains its weakly dissociated ion species while fully dissociated ion species are unretained. A suitable ion exclusion column is sold by Dionex Corporation under the name Ionpac ICE 6 column. The exclusion column 84 separates weakly dissociated species from strongly dissociated species in a sample plug. A typical ion exclusion column is in the form of a 9×250 mm column. The unretained components of the sample are routed to concentrator column 32 as in FIG. 1 for focusing the sample ions of interest as in the embodiment of FIG. 3. After the unretained species are eluted off of column 84 of valve 54, the valve is switched to the load mode or position in which detector cell effluent stream from detector 44 is routed in line 86 to valve 54, ports 50d and 50e through column 84, ports 54b and 54c, conduit 88 to an optional trap column 90 retains its weakly dissociated ionic species leaving a purified stream substantially devoid of weakly dissociated ions. This purified stream is then used as the regenerant stream or the regenerant flow channel of suppressor 42. This trap column is optional and useful if the weakly dissociated ionic species are of a type and concentration which would interfere with the analysis. Other operational parameters in the embodiment of FIG. 8 are similar in the prior embodiments.

The following examples illustrate different specific, non-limiting examples of the present invention.

Example 1

Figure 5:
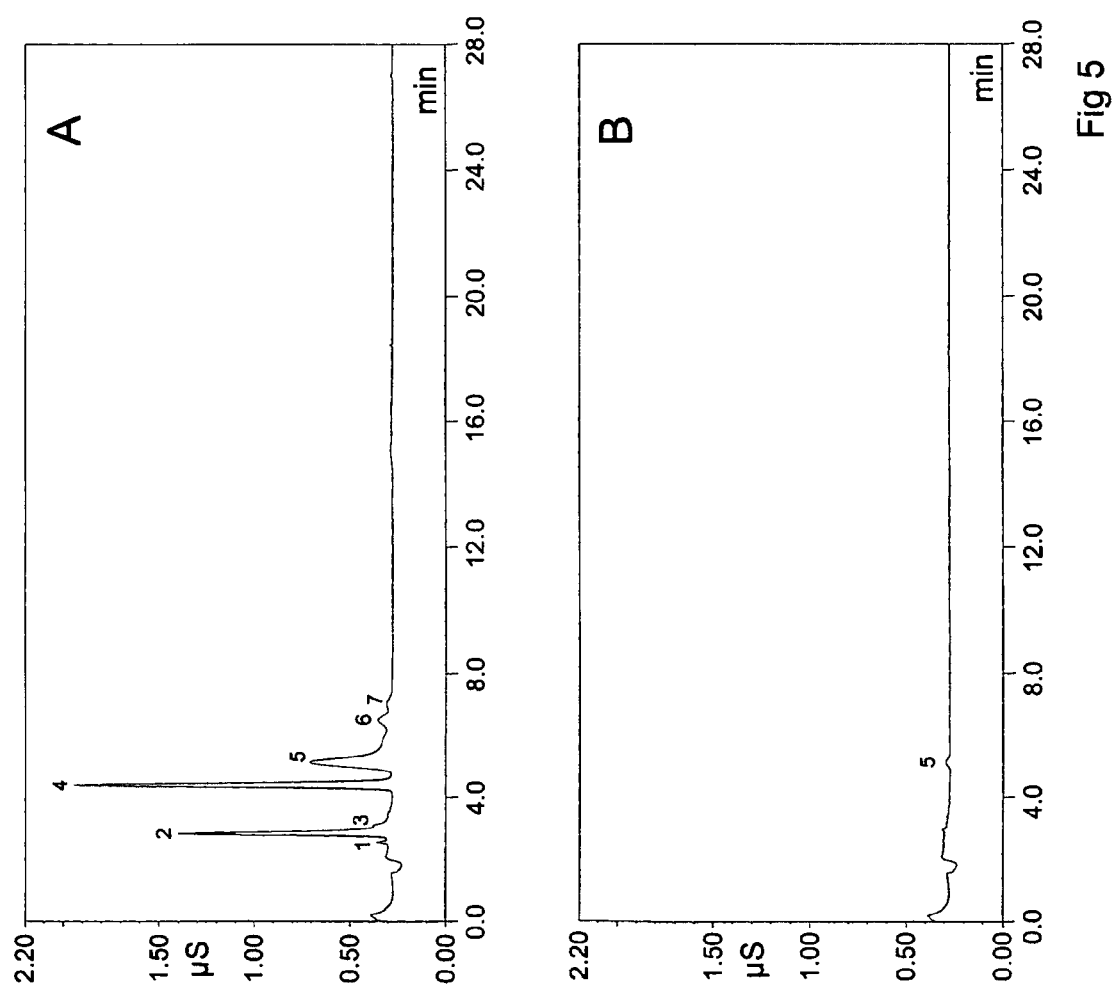
FIGS. 5, 9-11 are experimental results illustrating the present invention.

An apparatus of the type shown in FIG. 4 was used for neutralizing and analysis of a caustic sample (5% NaOH). A Dionex ICS 2500 Ion chromatograph was used in this setup with the required valve setup. A Dionex AS15 column was used in this analysis using a 35 mM NaOH eluent generated via an eluent generator. A 10 uL sample was injected into a neutralizer column (column packed with 8% cation exchange resin). The sample was neutralized as per the present invention and the neutralized sample was diverted to a concentrator column (TACLP1 4×35 mm from Dionex Corporation) using a DI water stream. The anions in the sample were retained and then analyzed. The resulting chromatogram is illustrated in FIG. 5 (Inset A). It shows analysis of the sample of the major anions as acetate (2), chloride (4), carbonate (5) sulfate (6) and oxalate (7). The blank run (inset B) shows the presence of a small amount of carbonate. These results suggest minimal contamination from the setup of the present invention. A single pump was used for the function of neutralization and analysis as per the present invention.

Example 2

Analysis of anions in acetic acid is shown in this example. It is difficult to analyze trace anions in the presence of the 5% matrix acetate ions. In this example an ion exclusion column is used to retain the matrix ions while the other fully dissociated ions are focused on a concentrator column 32 as shown in FIG. 8. The setup is similar to FIG. 8 with the exception that the cell effluent was not used for the function of regenerating the ion exclusion column rather the column was washed after the analysis with the flowing aqueous stream. In this example 100 mM Boric acid was dispensed by the pump 20 and was used to divert the sample through the ion exclusion column. The fully dissociated ions of interest were retained on the concentrator column (TACLP1 4×35 mm from Dionex Corporation). The Boric acid was pumped into the EGC cartridge to form 15 mM Potassium tetraborate anion which was used for the analysis using a 2 mm AS14 chemistry at 0.5 ml/min. The gradient used was

| Time | Gradient (KOH) |
|---|---|
| 0 | 5 |
| 10 | 5 |
| 16 | 30 |
| 20 | 30 |

The resulting chromatogram (FIG. 9) shows no interference from acetate (2) and it was possible to analyze for Fluoride (1) Chloride (3) and Sulfate (4) and as per the present invention both matrix elimination and eluent generation was accomplished using a single pump setup.

Example 3

Figure 10:
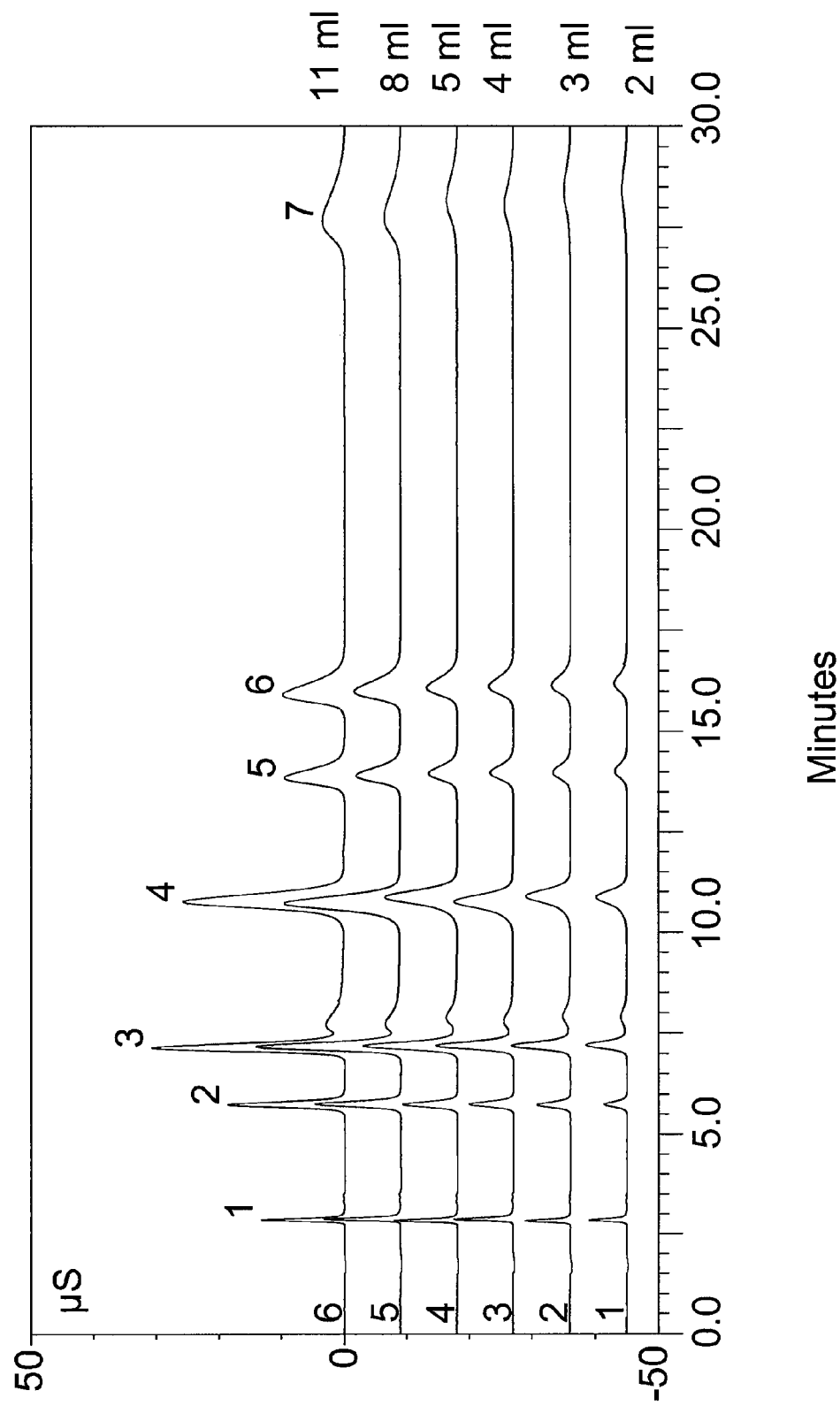
Figure 11:
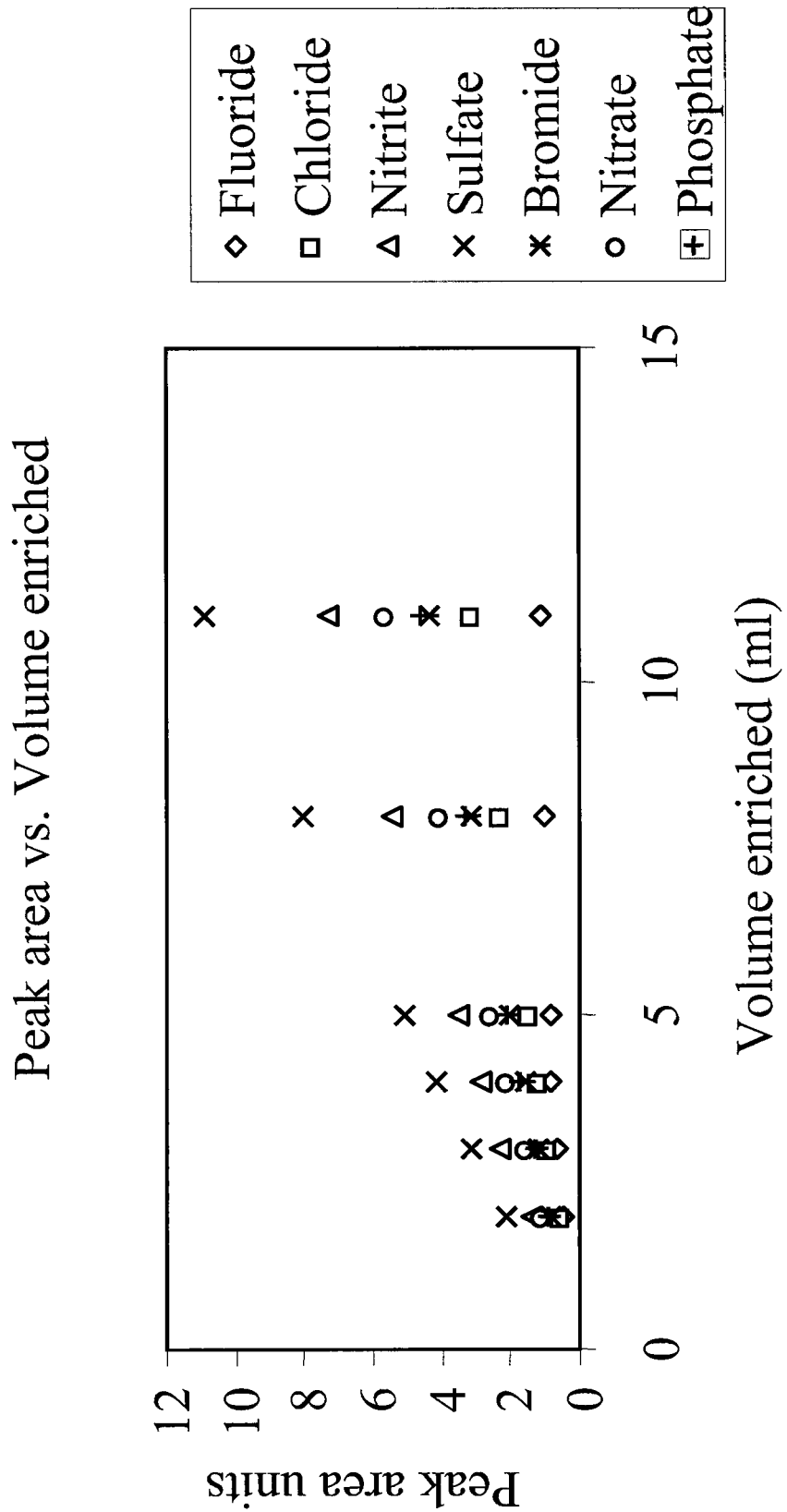

The setup in FIG. 1 was used for sample enrichment using an ICS 2500 system. A 1000× dilution of a standard 7 anion test mixture was used with a 1 ml loop. A TAC-LP1 concentrator column was used here to enrich the samples. The anions were analyzed using an AS15 column with 38 mM NaOH generated by an eluent generator module. The flow rate was 1.2 ml/min. FIG. 10 shows an overlay chromatogram of various sample volumes from 2 ml to 11 ml as per the present method. A plot of peak area versus volume enriched is shown in FIG. 11 for the seven anions and showed excellent linearity with correlation coefficients of 0.9999. The above example demonstrates the utility of the present invention for high sensitivity sample enrichment applications.

What is claimed is:

1. An ion chromatography method comprising:
   (a) flowing an aqueous liquid stream from an aqueous liquid source through a sample loop containing a liquid sample including ions of interest,
   (b) flowing the step (a) effluent through concentrator ion exchange medium in an ion concentrator to retain said sample ions,
   (c) flowing an eluent through said concentrator ion exchange medium to remove said retained sample ions in a concentrator effluent,
   (d) flowing the step (c) effluent through ion separation medium in an ion separator to separate said sample ions and form an ion separation effluent,
   (e) flowing the step (d) effluent past a detector to detect the separated sample ions, the flow in steps (a) through (d) being performed under pressure applied by a single pump, and
   (f) flowing an aqueous liquid stream from said aqueous liquid source through an eluent generator to generate the eluent of step (c) under pressure applied by said single pump.

2. The method of claim 1 further comprising, prior to step (c), repeating steps (a) and (b) to concentrate said sample ions in said concentrator.

3. The method of claim 1 further comprising:
   (g) suppressing the eluent in the step (d) effluent prior to step (e).

4. The method of claim 1 further comprising:
   (g) flowing, under pressure applied by said single pump, the effluent from step (e) through an ion removal device to form a deionized water stream which comprises said aqueous liquid source.

5. The method of claim 1 further comprising:
   (g) flowing the effluent from step (a) through an ion neutralizer prior to step (b).

6. The method of claim 1 further comprising:
   (g) prior to step (b), flowing the effluent from step (a) through a matrix elimination column, to retain matrix ions in said step (a) effluent.

7. The method of claim 1 further comprising:
   (g) prior to step (b), flowing the effluent from step (a) through a converter column to convert counterions of the sample ions to converted forms.

* * * * *